United States Patent [19]

Takesue

[11] 4,224,328

[45] Sep. 23, 1980

[54] METHODS WITH 1-SUBSTITUTED-4-ARYL-QUINAZOLIN-2(1H)-ONES AND THIONES AND PYRIDO[2,3-D]PYRIMIDIN-2-ONES AS PLATELET AGGREGATION INHIBITORS

[75] Inventor: Edward I. Takesue, Easton, Conn.

[73] Assignee: Sandoz, Inc., Hanover, N.J.

[21] Appl. No.: 29,552

[22] Filed: Apr. 11, 1979

Related U.S. Application Data

[63] Continuation of Ser. No. 747,919, Dec. 6, 1976, abandoned.

[51] Int. Cl.³ .................................... A61K 31/505
[52] U.S. Cl. ............................................ 424/251
[58] Field of Search ................. 424/251; 260/251 AB

[56] References Cited

U.S. PATENT DOCUMENTS

| | | | |
|---|---|---|---|
| 3,551,427 | 12/1970 | Ott | 260/251 AB |
| 3,723,432 | 3/1973 | Ott | 260/251 AB |
| 3,748,331 | 7/1973 | Cooke et al. | 260/251 AB |
| 3,764,600 | 10/1973 | Ott | 260/251 AB |
| 3,932,407 | 1/1976 | Beverung, Jr. et al. | 260/251 AB |

OTHER PUBLICATIONS

Weiss, H., "Progress in Hemostasis & Thrombosis," vol. 1, pp. 199–232 (1970).
Zucker, M., "Platelets, Drugs, & Thrombosis Syn.," Hamilton (1972), pp. 27–34.
Zucker et al., "J. Lab. Clin. Med.," vol. 76, No. 1 (1970), pp. 66–75.

*Primary Examiner*—Anna P. Fagelson
*Attorney, Agent, or Firm*—Gerald D. Sharkin; Richard E. Vila

[57] ABSTRACT

1-substituted-4-aryl-quinazolin-2(1H)-ones and thiones and pyrido[2,3-d]pyrimidin-2-ones, eg. 1-isopropyl-7-methyl-4-phenyl-quinazolin-2(1H)-one, are useful as platelet aggregation inhibitors.

24 Claims, No Drawings

METHODS WITH 1-SUBSTITUTED-4-ARYL-QUINAZOLIN-2(1H)-ONES AND THIONES AND PYRIDO[2,3-D]PYRIMIDIN-2-ONES AS PLATELET AGGREGATION INHIBITORS

This is a continuation of application Ser. No. 747,919 filed Dec. 6, 1976, now abandoned.

A wide variety of 1-substituted-4-aryl-quinazolin2(1H)-ones and thiones and pyrido[2,3-d]pyridin-2-ones have been heretofore found to possess anti-inflammatory, analgesic and anti-pyretic activity, see for example, U.S. Pat. Nos. 3,723,432, 3,748,331, 3,551,427, 3,758,475 and 3,764,600. I have now found that many such types of compounds have platelet aggregation inhibition activity and may be used for such purpose.

The compounds to be used as platelet aggregation inhibitors in accordance with the invention may be represented by the following formulae I and II:

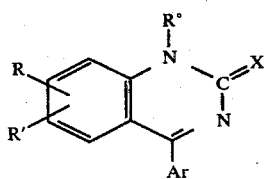

wherein
$R^O$ is alkyl of 1 to 6 carbon atoms, allyl, propargyl or cyclopropylmethyl,
R is hydrogen, alkyl of 1 to 4 carbon atoms, alkoxy of 1 to 4 carbon atoms, fluoro, chloro, bromo, nitro, amino, alkylthio of 1 to 4 carbon atoms, trifluoromethyl, N-alkylamino of 1 to 4 carbon atoms or N,N-dialkylamino in which each alkyl is of 1 to 4 carbon atoms,
R' is hydrogen, fluoro, chloro, bromo, alkyl of 1 to 4 carbon atoms or alkoxy of 1 to 4 carbon atoms, or
R and R' together form 6,7-methylendioxy,
X is oxygen or sulfur,
Ar is a group of the formula:

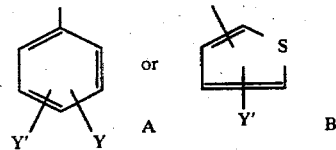

Y is hydrogen, fluoro, chloro, bromo, alkyl of 1 to 4 carbon atoms, alkoxy of 1 to 4 carbon atoms, hydroxy or trifluoromethyl, and
Y' is hydrogen, fluoro, chloro or alkyl of 1 to 4 carbon atoms,
with the provisos that: (1) R is other than amino or N-alkylamino when X is sulfur; and (2) R is hydrogen, fluoro, chloro, bromo, alkyl of 1 of 4 carbon atoms or alkoxy of 1 to 4 carbon atoms when Ar is a group of the formula B; and

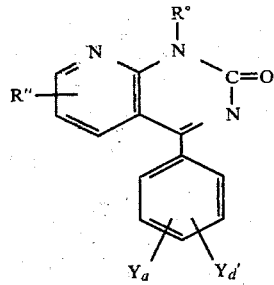

wherein
$R^O$ is as above defined,
each of $Y_a$ and $Y_a'$ is independently hydrogen, fluoro, chloro, alkyl of 1 to 4 carbon atoms or alkoxy of 1 to 4 carbon atoms, and
R" is hydrogen or alkyl of 1 to 4 carbon atoms.

The compounds of the formula I and II are mostly known but where not known may be prepared from available materials by methods known for the known compounds.

The compounds of the formulae I and II are useful in inhibiting blood platelet aggregation, for example in the treatment and prophylaxis of thrombosis and improving micro-circulation in mammals, as indicated by the inhibition of such aggregation caused in vitro by collagen in blood platelet-rich rabbit plasma (turbidimetric method in accordance with Born), and by the "ex-vivo" trial in rabbits involving oral administration of the test compound to rabbits which are exsanguinated 3 hours after the last administration, and the activity of the test compound is determined in vitro as described above. Inhibition commences at concentrations from about 1 μg/ml to about 30 μg/ml in the in vitro test.

For the above mentioned use, the dose will naturally vary depending on the compound employed, the mode of administration and the treatment desired. However, satisfactory results are obtained in warm-blooded animals at a daily dose of from about 1 to 50 mg/kg, conveniently given in divided doses 2 to 4 times a day, or in sustained release form. For the larger mammals, the daily dose is from about 50 to 1200 mg of the compound admixed with a solid or liquid pharmaceutical carrier for oral administration, and dosage forms typically contain from 12.5 to 600 milligrams, preferably 25 to 300 milligrams, of the compound in admixture with a solid or liquid pharmaceutical carrier for oral administration.

Pharmaceutical compositions containing a compound of the formula I or II may be formulated and prepared in a conventional manner and as previously disclosed in connection with the oral administration of the known compounds for anti-inflammatory use. The preferred compositions from the standpoint of ease of administration are solid compositions, particularly solid-filled gelatin capsules and tablets.

The generally preferred compounds of the formulae I and II are those in which $R^O$ is isopropyl. The more preferred compounds are those of the formula I in which Ar is phenyl or substituted phenyl, particularly phenyl or monofluorophenyl, and R is hydrogen, methyl, ethyl, methoxy or ethoxy with R' being hydrogen, or R and R' form 6,7-methylenedioxy. Within the above stated preferences X is preferably oxygen and R is in the 7-position when it represents a substituent.

Representative compounds of interest as platelet aggregation inhibitors in accordance with the present invention are:

(a) 1-isopropyl-7-methyl-4-phenyl-quinazolin2-(1H)-one.
(b) 1-isopropyl-7-methyl-4-(p-fluorophenyl)quinazolin-2(1H)-one.
(c) 1-isopropyl-6,7-methylenedioxy-4-phenylquinazolin-2(1H)-one.
(d) 1-isopropyl-6,7-methylenedioxy-4-(p-fluorophenyl)-quinazolin-2(1H)-one.
(e) 1-isopropyl-6,7-methylenedioxy-4-phenylquinazolin-2(1H)-thione.
(f) 1-isopropyl-6,7-methylenedioxy-4-(m-fluorophenyl)-quinazolin-2(1H)-one.
(g) 1-isopropyl-7-methyl-4-phenyl-quinazolin2(1H)-thione.
(h) 1-isopropyl-6-methoxy-4-phenyl-quinazolin2(1H)-one.
(i) 1-isopropyl-6-methoxy-4-phenyl-quinazolin2(1H)-thione.
(j) 1-isopropyl-7-methyl-4-phenyl-pyrido[2,3-d]pyrimidin-2(1H)-one.
(k) 1-isopropyl-5-methyl-4-phenyl-quinazolin2(1H)-one.
(l) 1-isopropyl-6,7-dimethyl-4-phenyl-quinazolin2(1H)-one.
(m) 1-isopropyl-7-methoxy-4-phenyl-quinazolin2(1H)-one.
(n) 1-isopropyl-7-methoxy-4-phenyl-quinazolin2(1H)-thione.
(o) 1-methyl-4-(2-thienyl)-quinazolin-2(1H)-one.
(p) 1-isopropyl-7-methyl-6-amino-quinazolin-2(1H)-one.
(q) 1-ethyl-4-phenyl-quinazolin-2(1H)-one.

A representative formulation for inhibiting platelet aggregation in prophylaxis of thrombosis and improving micro-circulation on administration 2 to 3 times a day is a capsule prepared by conventional techniques and containing the following:

| Ingredient | Amount (mg.) |
|---|---|
| 1-isopropyl-6,7-methylenedioxy-quinazolin-2(1H)-one. | 75 |
| Lactose | 225 |

What is claimed is:

1. The method of inhibiting platelet aggregation in mammals comprising administering orally to a mammal in need of such treatment a platelet aggregation inhibiting effective amount of a compound selected from the group consisting of compounds of the formula:

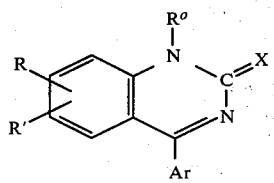

wherein
$R^o$ is alkyl of 1 to 6 carbon atoms, allyl, propargyl or cyclopropylmethyl,
R is hydrogen, alkyl of 1 to 4 carbon atoms, alkoxy of 1 to 4 carbon atoms, fluoro, chloro, bromo, nitro, amino, alkylthio of 1 to 4 carbon atoms, trifluoromethyl, N-alkylamino of 1 to 4 carbon atoms or N,N-dialkylamino in which each alkyl is of 1 to 4 carbon atoms,
R' is hydrogen, fluoro, chloro, bromo, alkyl of 1 to 4 carbon atoms or alkoxy of 1 to 4 carbon atoms, or
R and R' together form 6,7-methylenedioxy,
X is oxygen or sulfur,
Ar is a group of the formula:

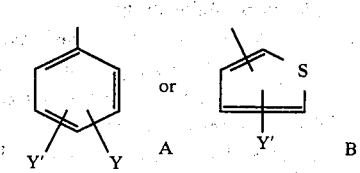

Y is hydrogen, fluoro, chloro, bromo, alkyl of 1 to 4 carbon atoms, alkoxy of 1 to 4 carbon atoms, hydroxy or trifluoromethyl, and
Y' is hydrogen, fluoro, chloro or alkyl of 1 to 4 carbon atoms,
with the provisos that: (1) R is other than amino or N-alkylamino when X is sulfur; and (2) R is hydrogen, fluoro, chloro, bromo, alkyl of 1 to 4 carbon atoms or alkoxy of 1 to 4 carbon atoms when Ar is a group of the formula B;
and compounds of the formula:

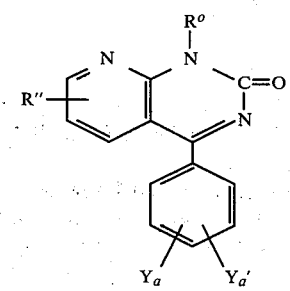

wherein
$R^o$ is as above defined,
each of $Y_a$ and $Y_a'$ is independently hydrogen, fluoro, chloro, alkyl of 1 to 4 carbon atoms or alkoxy of 1 to 4 carbon atoms, and
R'' is hydrogen or alkyl of 1 to 4 carbon atoms.

2. The method of claim 1 in which $R^o$ is isopropyl.

3. The method of claim 2 in which the compound is of the formula:

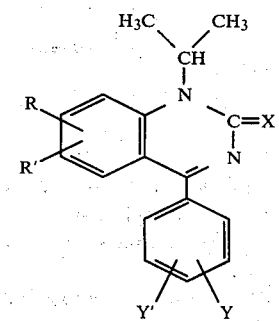

wherein X, R, R', Y and Y' are as defined.

4. The method of claim 3 in which Y is hydrogen or fluoro, Y' is hydrogen and either: (a) R is hydrogen, methyl, ethyl, methoxy or ethoxy with R' being hydrogen, or (b) R and R' together form 6,7-methylenedioxy.

5. The method of claim 4 in which X is oxygen and R is in the 7-position.

6. The method of claim 5 in which R and R' together represent 6,7-methylenedioxy.

7. The method of claim 5 in which R is methyl.

8. The method of claim 1 in which the compound is administered at a daily dose of from 50 to 1200 milligrams.

9. The method of claim 1 in which the compound is 1-isopropyl-7-methyl-4-phenyl-quinazolin-2(1H)-one.

10. The method of claim 1 in which the compound is 1-isopropyl-7-methyl-4-(p-fluorophenyl)-quinazolin-2(1H)-one.

11. The method of claim 1 in which the compound is 1-isopropyl-6,7-methylenedioxy-4-phenyl-quinazolin-2(1H)-one.

12. The method of claim 1 in which the compound is 1-isopropyl-6,7-methylenedioxy-4-(p-fluorophenyl)-quinazolin-2(1H)-one.

13. The method of claim 1 in which the compound is 1-isopropyl-6,7-methylenedioxy-4-phenyl-quinazolin-2(1H)-thione.

14. The method of claim 1 in which the compound is 1-isopropyl-6,7-methylenedioxy-4-(m-fluorophenyl)-quinazolin-2(1H)-one.

15. The method of claim 1 in which the compound is 1-isopropyl-7-methyl-4-phenyl-quinazolin-2(1H)-thione.

16. The method of claim 1 in which the compound is 1-isopropyl-6-methoxy-4-phenyl-quinazolin-2(1H)-one.

17. The method of claim 1 in which the compound is 1-isopropyl-6-methoxy-4-phenyl-quinazolin-2(1H)-thione.

18. The method of claim 1 in which the compound is 1-isopropyl-7-methyl-4-phenyl-pyrido[2,3-d]pyrimidin-2(1H)-one.

19. The method of claim 1 in which the compound is 1-isopropyl-5-methyl-4-phenyl-quinazolin-2(1H)-one.

20. The method of claim 1 in which the compound is 1-isopropyl-6,7-dimethyl-4-phenyl-quinazolin-2(1H)-one.

21. The method of claim 1 in which the compound is 1-isopropyl-7-methoxy-4-phenyl-quinazolin-2(1H)-one.

22. The method of claim 1 in which the compound is 1-isopropyl-7-methoxy-4-phenyl-quinazolin-2(1H)-thione.

23. The method of claim 1 in which the compound is 1-methyl-4-(2-thienyl)-quinazoline-2(1H)-one.

24. The method of claim 1, 9, 10 or 11 in which the compound is administered to a mammal in need of treatment prophylactically for thrombosis.

* * * * *